United States Patent [19]

Bertera

[11] Patent Number: 5,368,582
[45] Date of Patent: Nov. 29, 1994

[54] METHOD AND APPARATUS FOR INTRODUCING FLUID MATERIAL INTO AN EYE

[75] Inventor: James H. Bertera, Boston, Mass.

[73] Assignee: The Schepens Eye Research Institute, Boston, Mass.

[21] Appl. No.: 976,274

[22] Filed: Nov. 13, 1992

Related U.S. Application Data

[63] Continuation-in-part of Ser. No. 927,342, Aug. 10, 1992, abandoned.

[51] Int. Cl.$^5$ .................................................. A61M 35/00
[52] U.S. Cl. .................................. 604/295; 604/289; 604/294; 604/298; 604/300
[58] Field of Search ........................... 604/289–291, 604/294–296, 298, 300; 351/50–52; 417/207, 395; 128/DIG. 1, DIG. 7, DIG. 12, DIG. 26

[56] References Cited

U.S. PATENT DOCUMENTS

| | | | |
|---|---|---|---|
| 3,209,755 | 10/1965 | McCarthy et al. | 128/DIG. 26 |
| 3,934,585 | 1/1976 | Maurice . | |
| 4,480,259 | 10/1984 | Kruger et al. . | |
| 4,500,895 | 2/1985 | Buck et al. . | |
| 4,573,982 | 3/1986 | Forbes et al. | 604/300 |
| 4,623,337 | 11/1986 | Maurice . | |
| 4,878,646 | 11/1989 | Edelman et al. . | |
| 5,012,496 | 4/1991 | Weinreb et al. . | |
| 5,094,594 | 3/1992 | Brennan . | |
| 5,171,306 | 12/1992 | Vo | 604/295 |

FOREIGN PATENT DOCUMENTS

| | | |
|---|---|---|
| 0224352A1 | 6/1987 | European Pat. Off. . |
| 0483469A1 | 5/1992 | European Pat. Off. . |
| 2717578 | 11/1978 | Germany . |
| 2249405A | 5/1992 | United Kingdom . |

OTHER PUBLICATIONS

European Search Report issued on Dec. 28, 1993 in connection with related foreign application, International Application No. PCT/US 93/07488, filed on Aug. 9, 1993. (Attorney Docket No. ERM-86CP-PC). Vo Van Toi et al., The Association for Research in Vision and Ophthalmology Annual Meeting Abstract Issue (1992) vol. 33, No. 4.
TiNi Alloy Company, TiNi Pneumatic Valves (1992).
A. J. Rogers, "Ink Jet Takes Off", BYTE (1991) vol. 16.
Yokota et al., JSME International Journal, Series II (1991), vol. 34, No. 4, pp. 489–495.
Klebe, "Cytoscribing: A Method for Micropositioning Cells and Construction of Two-and Three-Dimensional Synthetic Tissues", (1988), Department of Cellular and Structural Biology, University of Texas Health Science Center, San Antonio, Texas 78023.
Thermal Ink–Jet Cartridge Designer's Guide, Hewlett Packard (1986).
Jaffee et al., "Color Hard Copy For Computer Systems", Proceed. of the SID (1983), vol. 24/3, pp. 219–234.
Tam et al., "Photoacoustic Ejection from a Nozzle (Pen) for Drop-On Demand Ink Jet Printing", Applied Optics (1982), vol. 21, No. 11, pp. 1891–1892.
Doane, "Methods of Ophthalmic Fluid Delivery", Clinical Pharmacology of the Anterior Segment (1980), vol. 20, No. 3, pp. 93–101.
Rev. Flynn et al., "Keratoconjunctivitis Sicca and New Techniques In Its Management", The Medical Journal of Australia, Jan. 14, 1976, vol. 1, No. 2, pp. 33–41.
Doane, "Mechanical Devices", International Ophthalmology Clinics, The Preocular Tear Film and Dry Eye Syndromes, (1973), vol. 13, No. 1, pp. 239–244.
Dohlman et al., "Mobile Infustion Pumps for Continuous Delivery of Fluid and Therapeutic Agents to the Eye", Annals of Opthalmology (Feb., 1971), pp. 126–128.

*Primary Examiner*—Randall L. Green
*Assistant Examiner*—P. Zuttarelli
*Attorney, Agent, or Firm*—Lahive & Cockfield

[57] ABSTRACT

A spectacle-like device mounts a system of pump elements that can project droplets of liquid onto a wearer's eye. A reservoir of the liquid and an electrical pump-controlling circuit are mounted on the spectacle frame for operation with the pump elements.

18 Claims, 5 Drawing Sheets

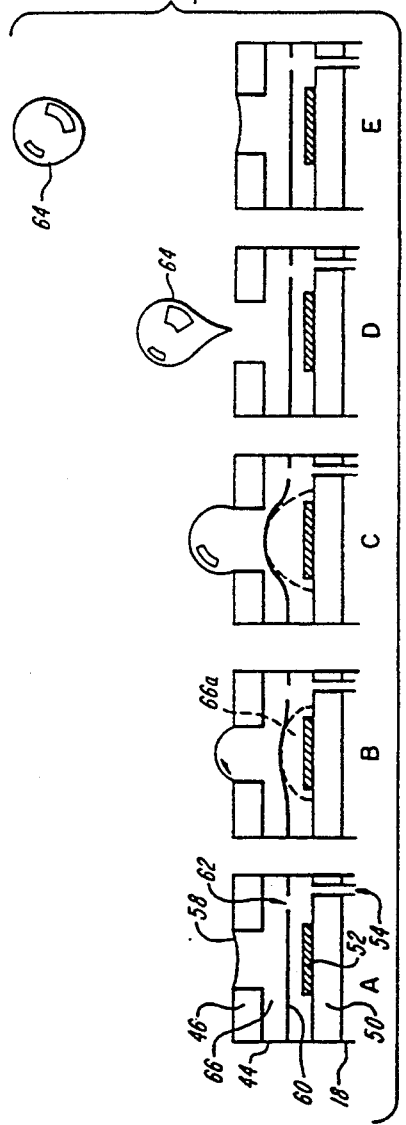
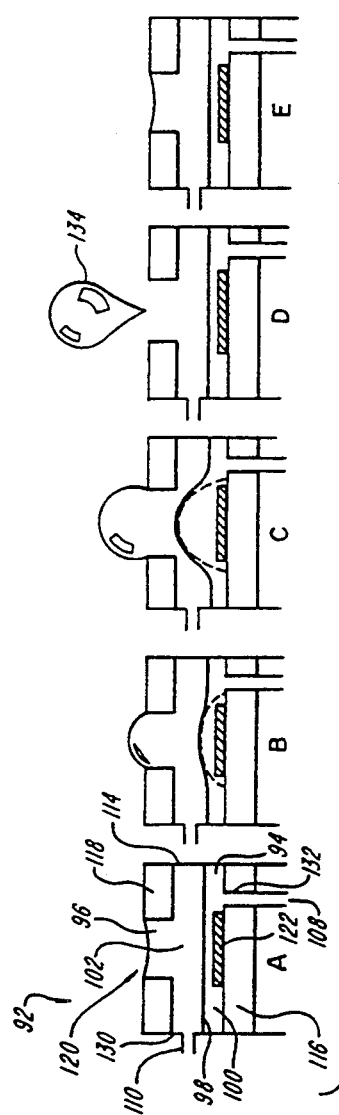

METHOD AND APPARATUS FOR INTRODUCING FLUID MATERIAL INTO AN EYE

This application is a continuation-in-part of the commonly-assigned application Ser. No. 07/927,342 filed Aug. 10, 1992 now abandoned.

BACKGROUND

This invention relates to devices for applying fluid to biological tissue and more particularly to apparatus which instills an aqueous solution into the eye. The invention has application, for example, as an unobtrusive and automatic device for introducing artificial tear fluid to relieve the discomfort and potential ocular damage caused by chronic dry eye condition, i.e., lachrymal deficiency. The invention also provides a corresponding method.

Many people suffer from a lack of eye moisture, resulting in discomfort and ocular damage. Even though available artificial tear solutions increase eye moisture and relieve discomfort, the application of an artificial tear solution provides only temporary relief. As a result, dry eye sufferers commonly apply artificial tear solution to their eyes repeatedly within the span of a day. The burden and interruption caused by frequent application of eye drops is a disincentive to applying the required dosages and to maintaining the proper moisture levels.

In addition to treating lachrymal deficiency, there is need for a device that introduces fluid into an eye to administer therapeutic agents that treat conditions such as corneal ulcerations. In these cases, an active medicinal agent is dissolved into a volume of fluid and administered to the eye. The applied fluid washes over the outer surface of the eye and thereby distributes the agent across the corneal surface. Introducing fluids having active medical ingredients to an eye requires careful control of the quantity of fluid administered. It generally is difficult, with the manual application of the fluid with an eye dropper, to control the number of drops introduced to the eye.

Some eye droppers exist that have a fluid chamber with a threaded piston that screws within a correspondingly threaded cylinder. The piston can be advanced within the cylinder by a selected number of threads and then held in position. By advancing the piston a predetermined amount, a corresponding predetermined volume of fluid is expelled from the chamber. Due to the mechanics involved, these devices are usually bulkier and more cumbersome than typical eyedroppers. This unwieldliness adds to the disincentive of a patient to apply a fluid.

Other devices have been developed that deliver fluid to an eye. These devices typically work by pumping fluid from a reservoir through a tube that has its distal end positioned adjacent to the eye. In some applications, the tube is surgically implanted under the skin; it begins at a fluid reservoir positioned, for example, at the lumbar region and ends adjacent the eye. These devices are cumbersome and invasive, and the mechanism needed to pump the fluid through the length of the tube is bulky and requires a heavy and bulky power source. Furthermore, control problems result from having to pump fluid to the eye through the relatively lengthy tube. Also, fluid flow within the tube can be disrupted by patient movement, and by inadvertent pinching or collapsing of the tube.

Portable eye irrigation systems have been developed which require the user to carry relatively cumbersome pump equipment and which offer limited flexibility and comfort. "Mechanical Devices", The Preocular Tear Film and Dry Eye Syndromes, Spring 1973, Vol 13, No. 1, describes several such devices. Typically, the prior systems have a single fluid outlet disposed in contact with each eye. Some systems have controls that provide adjustment to the delivered fluid volume, and some systems provide continuous irrigation.

Therefore, it is an object of this invention to provide apparatus which administers fluid to the eye in a controlled and compact fashion. An apparatus according to this object can offer a user comfort while delivering droplets or therapeutic mist to the eye.

It is another object of the present invention to provide an apparatus that is convenient to use for the sustained introduction of fluid into a person's eye.

It is a further object of the invention to provide an apparatus which provides relatively precise control over the quantity and frequency of fluid administered into an eye.

Another object of this invention is to provide an apparatus for introducing fluid into an eye and that is non-invasive and visually non-obstructive.

A further object of this invention is to provide an apparatus for introducing fluid into an eye with relatively low impact of fluid on the corneal surface of the eye.

Yet another object of this invention is to provide a facile method and apparatus for introducing fluid and therapeutic agents into an eye.

Other objects of the invention will be apparent from the description that follows.

SUMMARY OF THE INVENTION

The invention achieves the aforementioned objectives by providing, in one aspect, a device that introduces fluid to the corneal surface of the eye by having a pump element that projects droplets of the desired solution onto the eye. The pump element is fluidically coupled to a container of the solution. The coupled pump element and fluid container mount to a spectacle frame, and hence are positioned proximal to and in front of the eye. The pump element has a fluid outlet disposed adjacent to the eye and oriented so that fluid expelled from the outlet is directed at the corneal surface. A control circuit actuates the pump element to propel the solution from the fluid outlet into the air for travel to the eye.

A device for introducing fluid onto an eye as described above has application in relieving conditions involving lacrimal deficiency and in administering therapeutic fluids, i.e., drugs, to the surface of the eye. An artificial tear solution or a medicated fluid can be placed within the fluid container, and the user can activate the apparatus to deliver dosages of the fluid as selected with the control circuit. In particular, fluid from the container can be delivered to the pump for spraying onto the eye in minute increments. Upon actuation by a control signal generated by the control circuit, the pump element in one aspect delivers picoliter volumes of fluid to the eye. With a preferred type of pump, each picoliter volume is individually expelled from the fluid outlet as a discrete burst, spray or droplet of fluid. The fluid is ejected as a succession of droplets that travel through the air directly onto the corneal surface of the eye. Since the fluid is delivered in minute increments, i.e., picoliters, the invention attains fine control over the volume of fluid introduced into the eye.

The provision of both the applicator pump and the fluid outlet on a spectacle frame, in accord with the invention, attains superior performance. Further, the preferred pump element is immediately adjacent the fluid outlet, which enhances control of the droplet volume and discharge force. Also, the provision of both the pump and the outlet structure mounted together on the spectacle frame attains a high level of user convenience. It enables a person to use the device, and conversely remove it, with utmost ease. In a preferred embodiment, a reservoir of the fluid and the control circuit are also mounted on the spectacle frame, for further user convenience. The pump projects droplets into air for travel, unguided, to an ocular surface. The droplets preferably occur in succession with a controller selecting the duration or repetition rate.

A further feature of the invention is that the pump element preferably is a thermal expansion jet-type pump. The invention provides this type of pump combined with the liquid outlet in an exceedingly small and light-weight structure. An additional feature is a diaphragm-type member in the pump element to separate and thereby isolate, at least in part, the liquid being discharged to the wearer's eye from the liquid being heated for thermal expansion in the pump. Pumps of the thermal expansion jet-type are known for use in computer printers of the ink-jet type; U.S. Pat. No. 4,500,895 discloses one ink jet pump. Other thermal pumps can utilize laser energy to heat and expand working fluids, therapeutic fluids or absorbing elements.

It is also an advantage of this invention that patient safety is increased by providing a structure that is not surgically implanted and that does not come in physical contact with the eye. By the use of a pump that projects the liquid from an outlet, the invention removes the need to place fluid delivery tubes in contact with any tissue of the wearer, particularly tissue of the eye. The invention enhances patient safety and convenience by using soft flexible extension tubes to connect the fluid container to the pump element. The structure also imposes minimal restriction on the patient's field of view.

In another aspect, multiple fluid outlets, typically each with a separate pump, circumferentially surround the lens aperture of the eyeglasses to provide generally uniform fluid treatment to the eye. The fluid outlets disposed on the eyeglasses permit the unguided transmittal of fluid from the outlet through the air to the eye. Accordingly, the non-contact nature of the invention reduces the chance of infection as compared to devices disposed in contact with the eye. Such a device according to the invention is therefore useful in surgery requiring eye irrigation. Multiple pump outlets can surround a singular eye aperture, in this aspect, to efficiently irrigate the eye.

The invention also enchances the control for applying liquid to the eye. In some aspects according to the invention, both the rate of repetition and the volume of fluid droplets propelled from the pumps are programable and controllable.

In still other aspects, a method is provided for introducing fluid to the eye. An electrically controlled pump and fluid outlet are mounted to typical spectacle-like frames. The pump and fluid outlet are in fluid communication with a container which holds the fluid for application to the eye. An electrical signal is generated to activate the pump, thereby expelling the fluid from the container through the outlet and to the eye. The pump, in one practice of the invention, operates by pressurizing a fluid container causing controlled and pressurized ejection of fluid from the outlet into the air and toward the eye. In this aspect, the fluid outlet is preferrably a tapered tube with a jet or nozzle-like orifice placed near the eye, but not in contact with it.

In yet another aspect, the container holding the fluid is pressurized and maintained by micro-valves. Micro-valves, preferably at the fluid outlet orifice, control the release of fluid from the pressurized container in response to controlled electrical signals. Micro-valves employ piezoelectric cyrstals or shape-memory alloys, like TiNi.

In still other aspects, slender supports or stalks carry the pump element or micro-valve. A flexible stalk supporting a pump or micro-valve according to the invention greatly aids the control and delivery of fluid to an eye. For example, one stalk per eye affixed to a spectacle frame and carrying a small pump or micro-valve element can effectively and controllably irrigate the eye. In a separate configuration, a support structure with a stalk operates as a medicinal dispenser, a precise drug or chemical applicator, or a mist irrigator during surgical procedures.

These and other advantages of the invention will be more clearly understood by reference to the following detailed description and attached drawing, in which like reference numbers refer to like elements.

BRIEF DESCRIPTION OF THE DRAWING

FIG. 5 shows a succession of pictorial views A through E illustrating operation of a thermal expansion jet-type pump in the apparatus of FIG. 1.

FIGS. 7 and 8 are views similar to FIGS. 1 and 5, respectively, of a further embodiment of the invention.

DESCRIPTION OF ILLUSTRATED EMBODIMENTS

Figure 1:
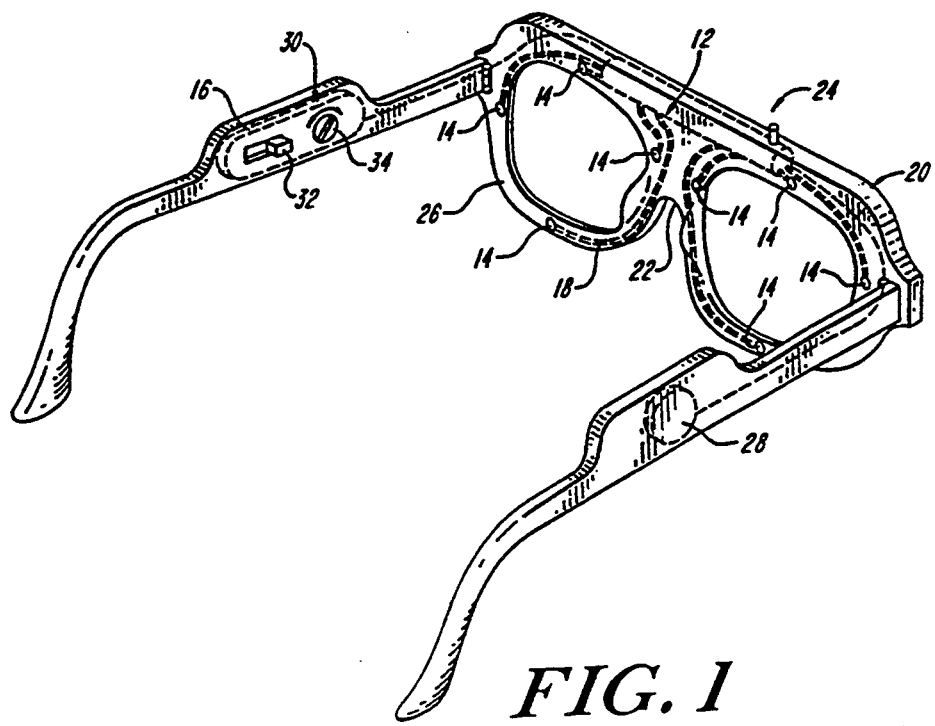
FIG. 1 is a pictorial view of apparatus for introducing fluid to an eye and embodying features of the invention.

One instillation device 10 according to the invention, shown in FIG. 1, has a pump mounted on a spectacle-like frame and which can project droplets of fluid onto the corneal surface of an eye. A patient wears the illustrated device like conventional spectacles, i.e., a pair of eyeglasses. The illustrated device 10 has a container 12 that holds a supply of fluid, an array of pumps 14 that project the fluid, a control module 16 that actuates the pumps 14, and fluid ducts 18 that fluidicly couple the pumps 14 to the container 12. All of these elements are carried on a spectacle-like support frame 20. The frame 20 can mount optical lenses and hence serve also as a pair of eyeglasses.

The instillation device 10 can apply, among other fluids, moisturing or medicating liquid to the topical surface of a patient's eye. The container 12 holds a supply of liquid and fluidicly connects with the pumps 14 by way of the fluid ducts 18. The ducts 18, as illustrated, preferably conform to the structure of the spectacle-like frame 20. The control module 16 produces electrical control signals that actuate the pumps 14 to expel fluid. Each pump 14 electrically connects to the control module 16 to receive a control signal. Each illustrated pump 14 is a thermal expansion jet-type pump.

Figure 2:
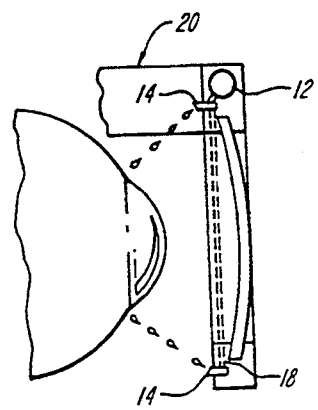
FIG. 2 is a pictorial view of fluid being introduced to an eye by a method embodying features of the invention.

The device 10 depicted in FIG. 1 is worn by the patient like conventional eye glasses. The frame 20 has an eye-piece 26 that rests on the bridge of the patient's nose and is held in position by two temple members that supportingly engage the patient's ears. As further shown in FIG. 1, a plurality of pumps 14 are disposed about the rim of each eye-piece 26 of the frame 20. Preferably the arrangement of the pumps 14 circumferentially surrounds the eyeglass aperture to apply fluid from the container 12 substantially uniformly over the surface of the eye. The frame 20 locates the pumps 14 adjacent to and spaced in front of the patient's eyes so that the pumps can project fluid into the air and toward the eye, as FIG. 2 shows. In the embodiment shown in FIG. 1, the eyepiece typically is positioned between 1 cm and 7 cm in front of the eye of the patient.

As shown in FIG. 2, each pump 14 preferably is oriented to direct liquid to a selected location or region on the outer corneal surface. The control module 16 actuates each pump 14 to expel fluid at a specified rate and volume, as explained further hereinafter.

Returning to FIG. 1, the illustrated container 12 is located on the frame 20 positioned above the frame nose piece 22. The container 12 has a fluid port 24 for filling and emptying. By way of example, the capacity of the illustrated container 12 is 10 ml to 20 ml.

The fluid conduits 18 extend from the container 12 to each pump 14. The illustrated conduits 18 are fluidicly sealed passages incorporated within the frame eye-piece 26.

Figure 3:
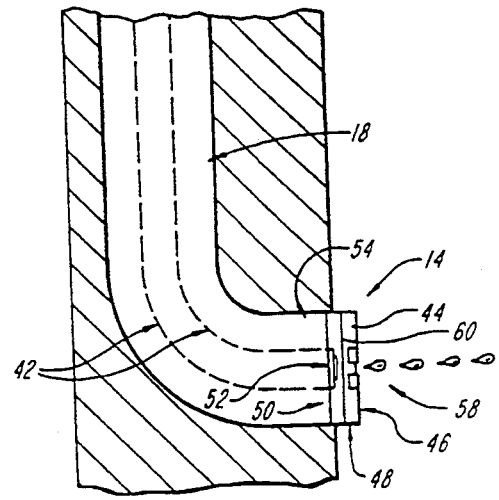
FIGS. 3 and 4 are simplified diagrammatic side and enlarged front views respectively of a pump for practice of the invention.
Figure 4:
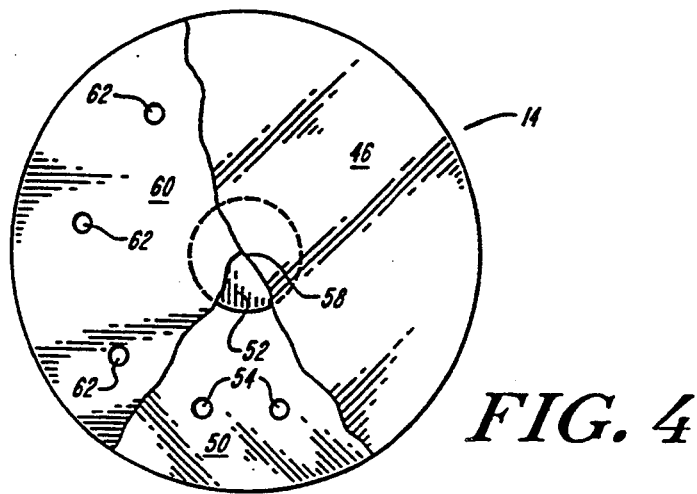

With reference to the diagrammatic views of FIGS. 3 and 4, each illustrated pump 14 has a chamber 44 that receives liquid to be dispensed from a fluid conduit 18. The pump dispenses the liquid from the chamber through a frontal fluid outlet 58. The illustrated pump chamber 44 is bounded by a back wall 50, a tubular side wall 48, and a front wall 46. The fluid outlet 58 is formed by a centrally-located aperture through the chamber front wall 46. The pump chamber 44 is mounted on the end of a fluid conduit 18 to receive fluid directly from the conduit through one or more small openings 54 through the chamber back wall 50.

The pump mechanism employs an electrical heater 52, typically a thin film electrical resistive element, located at the back of the chamber 44 and typically mounted on the chamber back wall 50 as illustrated. The heater 52 is aligned directly opposite the pump outlet 58 and is connected to the electrical control module 16 by way of electrical conductors 42.

As further shown in FIGS. 3 and 4, each illustrated pump 14 has a diaphragm 60, considered optional, that spans across the chamber 44 between the heating element 52 and the front wall 46 and that is apertured with one or more through passages 62 for the liquid being pumped. The diaphragm is flexible and secured, for example, to the chamber side wall 48. The apertures in the diaphragm 60 are not between the heating element 52 and the fluid outlet 58 but rather are radially spaced outwardly therefrom. The passages 62 in the illustrated diaphragm 60 are adjacent the periphery of the diaphragm, and the heating element 52 is located adjacent the center of the structure, as shown.

With further reference to FIG. 1, the control module 16 illustratively mounts on one temple piece of the frame 20 and operates all the pumps 14 concurrently and essentially in parallel. An alternative is to provide a control module 16 that produces a selected pattern of multiple signals for operating different pumps 14 selectively. The illustrated control module 16, FIG. 1, operates with a battery power source 28, illustratively carried on the other frame temple piece, and an adjustable pulse generator 30. An on-off switch 32 and a control adjustment 34 enable the user to turn the pumps off and on, and to vary the control signal to the pumps to control the fluid delivery to the eye. In particular, the control module 16 is preferably arranged so that the duration and the frequency of the control signal can be selectively adjusted. In one preferred practice, the control module operates each pump 14 to expel a succession of liquid droplets, and is controllable to select the duration of each succession of droplets and to select the interval between successions. The further construction of the control module 16 and its operation with the remaining elements of the system as described herein can be implemented with known skills.

In operation, and with references to FIGS. 1 and 3, liquid to be dispensed enters the chamber 44 from the fluid conduit 18 by way of the aperture 54 in the chamber back wall 50. The liquid passes through the openings 62 in the diaphragm 60 and hence normally substantially fills the chamber 44. The aperture forming the fluid outlet 58 is sufficiently small so that capillary forces retain the liquid within the chamber, and the liquid does not leak out under normal conditions. The pump discharges a droplet 64 of the liquid in response to an electrical signal applied from the control module 16 to the heater 52. The resultant thermal expansion of liquid adjacent the heater 52, within the chamber 44, produces a vaporizing force that expels a droplet outward from the chamber through the outlet 58.

The sequential views A through E of FIG. 5 depict this operation of the illustrated pump 14. FIG. 5A shows the pump at rest, with the chamber 44 filled with liquid 66 from the conduit 18 and a capillary meniscus at the outlet port 58. When the heater 52 becomes hot, due to an electrical signal from the control module 16, a bubble-like volume 66a of thermally expanded liquid forms adjacent the heater 52. The resultant increased pressure in the chamber 44 forces liquid outward through the fluid outlet 58, as appears in FIG. 5B.

FIG. 5C shows further development of the bubble-like volume 66a of thermally expanded fluid in front of the heater 52, and the correspondingly increased droplet formed at the pump fluid outlet 58. Upon further expansion of the liquid adjacent the hot heater 52, and termination of the heating signal to the heater 52 so that the thermal expansion in the liquid adjacent the heater 52 terminates, a drop 64 of the liquid is expelled outward from the outlet. FIG. 5E shows that the pump 14 quickly resumes the quiescent condition, similar to that of FIG. 5A with the ejected droplet directed toward the eye of the wearer of the device 10.

The operation of each pump 14, in response to an electrical impulse from the control unit 16, is essentially instantaneous through the successive stages shown in FIGS. 5B, 5C and 5D. The further construction of each pump 14, and its operation with the other elements of the system as described herein, can be implemented with known skills.

Another embodiment of the pump 14 employs a laser to heat and thereby expand the fluid in the chamber 44, FIGS. 3 and 5, in place of the resistive heating by heater 52. For example, a modulated laser beam which is absorbed and focussed at the liquid in chamber 44 will cause vaporization and ejection of fluid from outlet 58 at the the modulated frequency. Laser power and wavelength and can be used to vary the volume of ejected liquid.

In one illustrative embodiment, the pump parameters, including the chamber 44 volume and the outlet port 58 and the heating element 52, are selected to form each droplet with a size typically in the order of 200 picoliters. This volume is illustrative and the invention can be practiced with other parameters. By way of example, in one practice, the pumps 14 of the device 10 of FIG. 1 deliver 200 picoliter volumes of artificial tear fluid at a rate of 100 Hz for one second of every five second interval. Typically, repetition rates between 1 and 2000 Hz are selected depending upon the fluid viscosity. These frequencies are used in conjunction with outlet apertures generally between 10 and 100 $\mu$m to deliver, for example, 1 microliter per minute tear delivery, which is normal.

The optional diaphragm 60 in the pump chamber 44, FIGS. 3 and 4, can be a thermal barrier between the liquid that is dispensed from the outlet 58 and the liquid that is thermally expanded by the heater 52. The diaphragm can thus assure that the liquid the pump expels is relatively cool, and is not the hotter liquid acted on by the heater 52.

Figure 6:
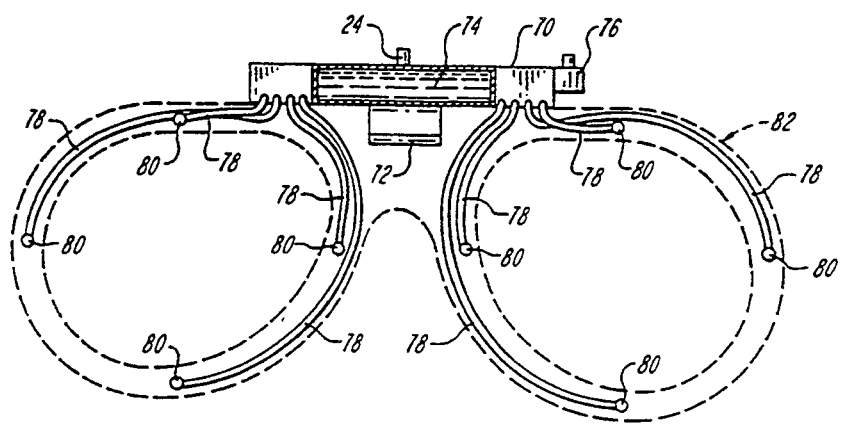
FIG. 6 is a pictorial view, partly disassembled, of an alternative apparatus for introducing fluid to an eye according to further features of the invention.

Among other variations with which the invention can be practiced are, as shown in FIG. 6, a dispenser 70 that provides a system of pumps 80 connected by way of positioning tubes 78, like stalks, with a liquid container 74 and further having a control module 76. The dispenser 70 has a mounting clamp 72 for removable and replaceable mounting on a spectacle frame 82. Each pump 80 of the illustrated dispenser 70 is mounted on the distal end of a positioning tube 78. Each positioning tube preferably can be selectively flexed to position and orient the pump outlet port as desired relative to the eye of the user of the device. Each positioning tube 78 is relatively soft and readily deformed to assure that inadvertent contact of a tube or pump with the user causes no injury.

The dispenser 70, aside from being removable and replaceable relative to a spectacle frame 82, can be otherwise identical to the device 10 described above with reference to FIGS. 1 through 3.

Note that the liquid container 12 of the device 10 of FIG. 1 and the container 74 of the FIG. 6 dispenser 70 can be a removable and replaceable cartridge. In this alternative arrangement, the user simply fits a new cartridge of the selected liquid to the device, rather than refilling the container. When a cartridge is emptied of liquid, it is simply removed and replaced. This construction enables a device according to the invention to dispense different liquids, both with and without selected medications, as required by the medical needs of the user.

Figure 7:
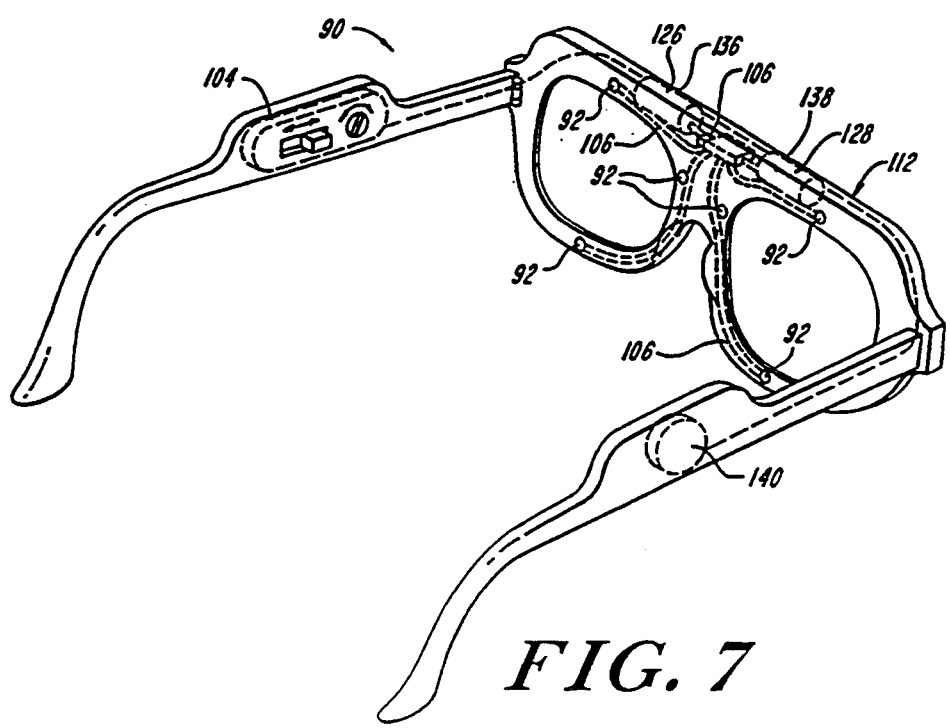

FIG. 7 shows the structure and operation of another device 90 in which, as shown in FIG. 8, a flexible diaphragm element 98 forms two fluidicly isolated chambers 94 and 96 in each pump 92. The two chambers can contain two different fluids 100 and 102. More particularly, a rear chamber 94 can contain a fluid that is optional for the liquid-ejecting pumping operation, and a forward chamber 96 can contain a treatment fluid to be ejected to the wearer's eye.

Figure 7A:
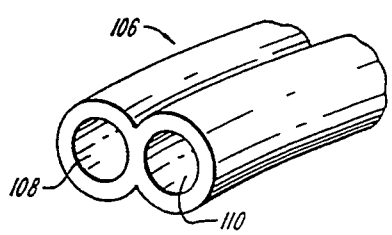
FIG. 7A is a detail view of a duct for use therein.

The device 90, depicted in FIG. 7, is in part similar in construction and operation to the device 10 of FIGS. 1–5. The device 90 has an array of pumps 92 that project fluid, a control module 104 that actuates the pumps 92, and a fluid duct 106 that has two isolated fluid passages 108 and 110, as illustrated in FIG. 7A, for carrying fluid to the pumps 92. These elements are carried on a spectacle-like frame 112 that is worn by the patient like a conventional pair of eyeglasses.

As depicted in FIG. 8, each illustrated pump 92 is a thermal expansion jet-type pump and has a cylindrical sidewall 114 that is bounded by a backwall 116 and a front wall 118. The front wall 118 has a centrally-located aperture that forms a fluid outlet port 120. The pump employs an electrical heater 122, typically a thin film electrical resistive element mounted on the backwall 116 aligned opposite the fluid outlet port 120, and connected to the electrical control module 104 by way of electrical conductors (not shown).

As further shown in FIGS. 7, 7A, and 8, the device 90 has two separate containers 126 and 128 that each hold a supply of fluid. Each supply of fluid is coupled to one of the isolated passages 108 and 110 of the fluid duct 106. In the illustrated device, the container 126 is fluidicly connected to the passage 108 and the container 128 is fluidicly connected to the passage 110. The duct 106 couples the fluids in the containers 126 and 128 to the chambers of the pumps 92.

Each illustrated pump 92, shown in FIG. 8, has a diaphragm 98 that spans the interior of the pump 92 and seals to the sidewall 114 to form a flexible, non-permeable barrier between the chambers 94 and 96. Each chamber couples to only one fluid passage of the fluid duct 106. In the illustrated example, the forward chamber 96 has a fluid port 130 in the sidewall 114 that couples to the passage 110 to receive fluid 102 from the container 128. Likewise, the rear chamber 94 receives fluid 100 from the container 126 through a fluid port 132 that extends through the backwall 116 and is coupled to the fluid passage 108.

Referring again to FIG. 8, the sequentially illustrated operation of pump 92 commences as shown in FIG. 8A with the pump at rest, with the back chamber 94 filled with the fluid 100 from the duct 108 that is fluidicly coupled to the container 126, and with the front chamber 96 filled with the fluid 102 from the duct 110 that is fluidicly coupled to the container 128. When the heater 122 becomes hot, due to an electrical signal from control module 104, the fluid 100 within the back chamber 94 expands, FIGS. 8B and 8C. The resultant increased pressure in the chamber 94 forces a drop 134 of the fluid 102 in the chamber 96 outward through the fluid outlet 120, appears in FIG. 8D. FIG. 8E shows that the pump 92 quickly resumes the quiescent condition, similar to that of FIG. 8A, with the ejected droplet 134 directed toward the eye of the wearer of the device 90, and with the forward chamber 96 again filled with the treatment liquid 102.

Another embodiment uses a heater 122 that is heated by laser energy to transfer vaporizating energy to the working fluid 100. A laser beam focussed at the element 122 can thereby provide operating power for the pump operation that FIG. 8 illustrates.

In another embodiment, and referring to FIG. 1, the container 12 includes at least part of the mechanism for pumping fluid. For example, a piezoelectric crystal is coupled with the container 12 and operated by the control module 16 to create a modulated hydraulic pressure within the container 12 to eject fluid from each outlet 14. A programmable control module 16, for instance, enabled by a microprocessor chip, can vary the volume and the frequency of the ejected liquid by varying the frequency and amplitude of the drive signal to the piezoelectric crystal. Accordingly, only one pump mechanism is required for multiple outlets 14. Preferably, the fluidic tube 18 leading to each outlet 14 is tapered at the end to form a jet orifice to aid the fluidic ejection to the eye.

The configuration shown in FIG. 1 can be embodied in still another way by installing a pressurized container 12. A micro-valve positioned at the fluid outlet of the container 12, or at each outlet 14, can replace the pumping mechanisms shown, for example, in FIG. 5. A piezoelectric crystal, which expands and contracts in response to a drive signal from control module 16, can operate as a micro-valve by releasing the pressurized fluid from the container 12. A TiNi pneumatic valve can similarly operate as a micro-valve. TiNi valves utilize a thin membrane of shape-memory alloy which normally closes the valve in a de-energized state. When the membrane is energized by responding to the control module 16, the membrane contracts and opens the valve.

Figure 9:
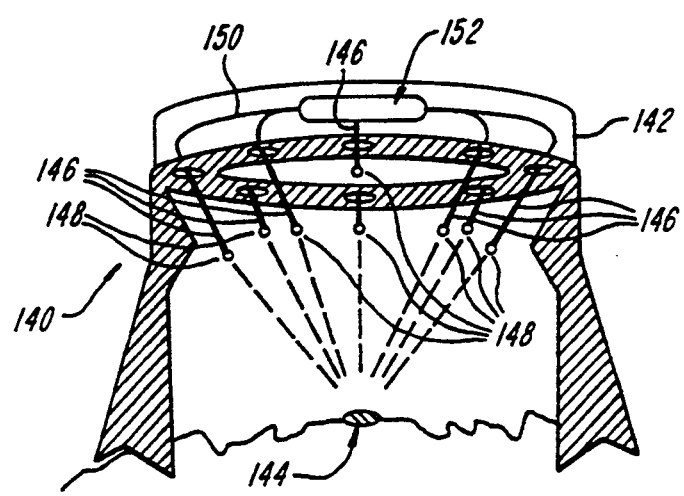
FIG. 9 is a pictorial view of a further embodiment of the invention, for delivering liquid to an eye during, for example, a surgical procedure.

One further practice according to the invention, is to control independently the pumps mounted about a single eye piece rim, to provide independent control of the rate and quantity of fluid delivered to each eye. FIG. 9 shows a liquid-spraying device 140, here shown as an aperture ring-like support 142 with multiple stalks 146. The illustrated support 142 includes support legs for resting away from and centered over the eye 144. Multiple stalks 146 mount to the support 142, each with an associated fluid outlet 148 disposed at the distal end, and directed toward the eye 144. Each stalk 146 and outlet 148 is connected through fluid lines 150 to a container 152 which holds the fluid for application to the eye. The container 152, fluid lines 150, and stalks 146 can, in one embodiment, mount to support 142 replaceably. The support 142 also houses a control module (not shown) for providing a control signal to the pumps. The control module can be similar to the corresponding element 16 of the FIG. 1 device 10. The fluid outlets 148 preferably operate as a pump, for example as a thermal jet pump, or can use micro-values in combination with a pressurized or hydraulically actuated container, as described above. This embodiment can, for instance, be effectively used to administer fluid to the eye during surgery requiring eye irrigation. A singular eye piece rim placed over the eye employs the teachings of the invention to effectively irrigate an eye, and surrounding area, under surgery.

It will be apparent that the embodiments of FIGS. 1, 6, and 7 can employ stalks similar to the stalks 146 of FIG. 9. The stalks for that practice, which are preferably sufficiently flexible to avoid injury to the eye, can dispose each fluid outlet or orifice closer to the eye than mounting them directly on the spectacle frame.

A further embodiment employs a set of one or more stalks 146 (FIG. 9), each with a pump element or valved outlet and each mounting a fluid outlet. This device provides irrigation, or application of drugs, toxic treatment chemicals, or growth inhibitors, with precise spatial control, as well as with the control of the droplet stream as discussed with the illustrated embodiments.

It will thus be seen that the invention efficiently attains the objects set forth above, among those made apparent from the preceding discussion and the drawings. In particular, the invention provides methods and apparatus for directing an air-borne liquid stream or succession of drops into the eye. Since certain changes may be made in the above construction without departing from the scope of the invention, it is intended that all matter contained in the above description or shown in the accompanying drawings be interpreted as illustrative rather than in a limiting sense. One such change is to mount the electrical control module and the battery separate from the spectacle frame that carries the pump and the fluid outlets; illustratively in a pocket or on a waist strap of the wearer. A reservoir of the liquid being dispensed can also be mounted separately from the spectacle frame; it preferably is under pressure to deliver the liquid, against the force of gravity, to the spectacle-mounted pump element.

It is also to be understood that the following claims are to cover all of the generic and specific features of the invention as described herein, and all statements of the scope of the invention which, as a matter of language, might be said to fall therebetween.

Having described the invention, what is claimed as new and secured by the Letters Patent is:

1. Apparatus for the topical introduction of liquid to the eye of a person wearing a spectacle-like frame, said apparatus comprising
    (A) a container for liquid that is to be introduced to the eye of the person,
    (B) at least one pump means having a fluid outlet and coupled with said container to receive liquid therefrom and arranged for mounting with said container on a spectacle-like frame with said outlet directed toward and spaced away from the eye,
        said pump means being operable in response to a control signal for propelling liquid, received from said container, from said outlet and toward the eye,
    (C) control means for generating said control signal and connected for applying said control signal to said pump means, said control means being arranged for mounting on the spectacle-like frame, and
    (D) pump positioning means for positioning said pump means and said outlet proximate to the eye and connected in fluid communication between said container and said pump means, said positioning means being elastically displaceable upon inadvertent contact with the eye, for protecting the eye.

2. Apparatus for the topical introduction of liquid to the eye of a person wearing a spectacle-like frame, said apparatus comprising
    (A) a container for liquid that is to be introduced to the eye of the person,
    (B) at least one expansion-type jet pump having a fluid outlet and coupled with said container to receive liquid therefrom and arranged for mounting with said container on the spectacle-like frame with said outlet directed toward and spaced away from the eye, said pump expanding fluid within said pump and being operable in response to a control signal for driving fluid, received from said container, through said fluid outlet and toward the eye, and (C) control means for generating said control signal and connected for applying said control signal to said pump, said control means being arranged for mounting on the spectacle-like frame.

3. Apparatus for the topical introduction of liquid to the eye of a person wearing a spectacle-like frame, said apparatus comprising (A) a container tier liquid that is to be introduced to the eye of the person, (B) at least one pump means having a fluid outlet and coupled with said container to receive liquid therefrom and arranged for mounting with said container on the spectacle-like frame with said outlet directed toward and spaced away from the eye, said pump means being operable in response to a control signal for propelling liquid, received from said container, from said outlet and toward the eye, and (C) control means for generating said control signal and connected for applying said control signal to said pump means, said control means being arranged for mounting on the spectacle-like frame, said control means producing said control signal to eject successive droplets of liquid from said fluid outlet, said control means being arranged for generating said control signal for producing said succession of droplets with selected duration and repetition, for controlling the quantity and rate of liquid introduced to the eye, said rate being in the range of one to two thousand Hertz.

4. Apparatus for the topical introduction of liquid to the eye of a person wearing a spectacle-like frame, said apparatus comprising (A) a container for liquid that is to be introduced to the eye of the person, (B) at least one pump means having a fluid outlet and coupled with said container to receive liquid therefrom and arranged for mounting with said container on the spectacle-like frame with said outlet directed toward and spaced away from the eye, said pump means being operable in response to a control signal for propelling liquid, received from said container, from said outlet and toward the eye, and (C) control means for generating said control signal and connected for applying said control signal to said pump means, said control means being arranged for mounting on the spectacle-like frame, said control means producing said control signal to eject successive droplets of approximately two hundred picoliters of liquid from said fluid outlet, said control means being arranged for generating said control signal for producing said succession of droplets with selected duration and repetition, for controlling the quantity and rate of liquid introduced to the eye.

5. Apparatus for the topical introduction of liquid to the eye of a person wearing a spectacle-like frame, said apparatus comprising (A) a container for liquid that is to be introduced to the eye of the person, (B) at least one pump means having a fluid outlet and coupled with said container to receive liquid therefrom and arranged for mounting with said container on the spectacle-like frame with said outlet directed toward and spaced away from the eye, said pump means being operable in response to a control signal for propelling liquid, received from said container, from said outlet and toward the eye, and (C) control means for generating said control signal and connected for applying said control signal to said pump means, said control means being arranged for mounting on the spectacle-like frame, said control means producing said control signal to eject successive droplets of liquid from said fluid outlet, said control means being arranged for generating said control signal for producing said succession of droplets with selected duration and repetition, for controlling the quantity and rate of liquid introduced to the eye, said control means being arranged for producing said control signal intermittently and wherein said rate is approximately one to two thousand Hertz.

6. Apparatus for the topical introduction of liquid to the eye of a person wearing a spectacle-like frame, said apparatus comprising (A) a container for liquid that is to be introduced to the eye of the person, (B) multiple pump means circumferentially disposed around at least one lens aperture of the spectacle-like frame, each of said pump means having a fluid outlet and coupled with said container to receive liquid therefrom and arranged for mounting with said container on the spectacle-like frame with said outlet directed toward and spaced away from the eye, said pump means being operable in response to a control signal for propelling liquid, received from said container, from said outlet and toward the eye, and (C) control means for generating said control signal and connected for applying said control signal to said pump means, said control means being arranged for mounting on the spectacle-like frame.

7. Apparatus for the topical introduction of liquid to the eye of a person wearing a spectacle-like frame, said apparatus comprising (A) a container for liquid that is to be introduced to the eye of the person, (B) at least one pump means having a fluid outlet and coupled with said container to receive liquid therefrom and arranged for mounting with said container on the spectacle-like frame with said outlet directed toward and spaced away from the eye, said pump means comprising at least one piezoelectric crystal for creating hydraulic pressure inside said container and being operable in response to a control signal for presurizing said container to propel liquid through said outlet and toward the eye, and (C) control means for generating said control signal and being connected for applying said control signal to said pump means.

8. Apparatus for the topical introduction of liquid to the eye of a person wearing spectacle-like frame, said apparatus comprising (A) a pressurized vessel containing liquid that is to be introduced to the eye of the person, (B) at least one valve means having a fluid outlet and coupled with said vessel to control liquid therefrom and arranged for mounting with said vessel on the spectacle-like frame with said outlet directed toward and spaced away from the eye, said valve means comprising a micro-valve having a piezoelectric crystal actuator and being operable in response to a control signal for releasing liquid from said pressurized vessel to eject liquid through said outlet and toward the eye, and (C) control means for generating said control signal and being connected for applying said control signal to said pump means.

9. Apparatus for the topical introduction of liquid to the eye of a person wearing a spectacle-like frame, said apparatus comprising (A) a pressurized vessel containing liquid that is to be introduced to the eye of the person, (B) at least one valve means having a fluid outlet and coupled with said vessel to control liquid therefrom and arranged for mounting with said vessel on the spectacle-like frame with said outlet directed toward and spaced away from the eye, said valve means comprising a shape-memory alloy for creating a micro-valve and being operable in response to a control signal for releasing liquid from said pressurized vessel to eject liquid through said outlet and toward the eye, and (C) control means for generating said control signal and being connected for applying said control signal to said pump means.

10. Apparatus according to claim 9 wherein said shape memory alloy is TiNi.

11. Apparatus for the topical introduction of liquid to the eye of a person wearing a spectacle-like frame, said apparatus comprising (A) a container for liquid that is to be introduced to the eye of the person, (B) at least one pump means having a fluid outlet and coupled with said container to receive liquid therefrom and arranged for mounting with said container on the spectacle-like frame with said outlet directed toward and spaced away from the eye, said pump means having heating means and being operable in response to a control signal for thermally expanding fluid and for expelling liquid, received from said container, through said fluid outlet and toward the eye, and (C) control means for generating said control signal and connected for applying said control signal to said pump means, said control means being arranged for mounting on the spectacle-like frame.

12. Apparatus according to claim 11 wherein said heating means includes a thin film resistor element.

13. Apparatus according to claim 11 further comprising means for separating liquid being discharged from said fluid outlet from the thermally expanded fluid.

14. Apparatus according to claim 11 wherein said heating means includes a laser source for delivering thermal energy to said fluid.

15. Apparatus according to claim 11 wherein said heating means includes a laser source and an absorbing element, said laser source being arranged for heating said absorbing element and said absorbing element is arranged for heating fluid by conduction.

16. Apparatus for the topical introduction of liquid to the eye of a person wearing a spectacle-like frame, said apparatus comprising (A) a container for liquid that is to be introduced to the eye of the person, (B) at least one pump means having a fluid outlet and coupled with said container to receive liquid therefrom and arranged for mounting with said container on the spectacle-like frame with said outlet directed toward and spaced away from the eye, said pump means including a thermal expansion-type jet pump and being operable in response to a control signal for thermally expanding fluid and for expelling liquid, received from said container, through said fluid outlet and toward the eye, said expansion-type jet pump having diaphragm means disposed between the thermally expanded fluid and said fluid outlet, and (C) control means for generating said control signal and connected for applying said control signal to said pump means, said control means being arranged for mounting on the spectacle-like frame.

17. Apparatus according to claim 16 in which said diaphragm means forms a first pump chamber in which fluid is expanded for pumping action and forms a second pump chamber contiguous with said first chamber and from which fluid is discharged in response to said pumping action.

18. Apparatus according to claim 17
in which said container is coupled for applying liquid therein to said second pump chamber, and
further comprising a second container for fluid and coupled with said first pump chamber.

* * * * *